US012648695B2

(12) United States Patent
Hu et al.

(10) Patent No.: US 12,648,695 B2
(45) Date of Patent: Jun. 9, 2026

(54) FUNDUS CAMERA AND FULLY-AUTOMATIC PHOTOGRAPHY METHOD FOR FUNDUS IMAGE

(71) Applicant: SHANGHAI EAGLEVISION MEDICAL TECHNOLOGY CO., LTD., Shanghai (CN)

(72) Inventors: Dingshan Hu, Shanghai (CN); Xinqiang Pang, Shanghai (CN); Xin Jiang, Shanghai (CN); Hanyue Guo, Shanghai (CN); Wenbin Ren, Shanghai (CN); Xiangang Chang, Shanghai (CN); Peng Wang, Shanghai (CN); Yubo Wei, Shanghai (CN); Chao He, Shanghai (CN); Dalei Zhang, Shanghai (CN)

(73) Assignee: SHANGHAI EAGLEVISION MEDICAL TECHNOLOGY CO., LTD., Shanghai (CN)

( * ) Notice: Subject to any disclaimer, the term of this patent is extended or adjusted under 35 U.S.C. 154(b) by 507 days.

(21) Appl. No.: 18/031,513

(22) PCT Filed: Jan. 27, 2021

(86) PCT No.: PCT/CN2021/073875
§ 371 (c)(1),
(2) Date: Apr. 12, 2023

(87) PCT Pub. No.: WO2022/077800
PCT Pub. Date: Apr. 21, 2022

(65) Prior Publication Data
US 2023/0404401 A1 Dec. 21, 2023

(30) Foreign Application Priority Data
Oct. 14, 2020 (CN) .......................... 202011095133.3

(51) Int. Cl.
*A61B 3/15* (2006.01)
*A61B 3/12* (2006.01)

(52) U.S. Cl.
CPC ................ *A61B 3/152* (2013.01); *A61B 3/12* (2013.01)

(58) Field of Classification Search
CPC ......... A61B 3/152; A61B 3/12; A61B 3/0025; A61B 3/14; A61B 3/0008; A61B 2560/0431
(Continued)

(56) References Cited

U.S. PATENT DOCUMENTS

| | | |
|---|---|---|
| 2005/0275804 A1 | 12/2005 | Masaki |
| 2019/0110677 A1 | 4/2019 | Walsh et al. |
| 2020/0121185 A1* | 4/2020 | Lee ........................ A61B 3/152 |

FOREIGN PATENT DOCUMENTS

| | | |
|---|---|---|
| CN | 1810202 A | 8/2006 |
| CN | 103908221 A | 7/2014 |

(Continued)

OTHER PUBLICATIONS

International Search Report for PCT/CN2021/073875 mailed on Jun. 30, 2021.
(Continued)

*Primary Examiner* — William R Alexander
*Assistant Examiner* — Alaina Marie Swanson
(74) *Attorney, Agent, or Firm* — The PL Law Group, PLLC

(57) ABSTRACT

A fully-automatic photography method for a fundus image includes moving a lens of the fundus camera to align with the pupil, controlling the lens to approach the eyeball and capturing an image, the image being formed by an illuminating beam reflected by the cornea, determining a working distance by using the image, adjusting the focal length,
(Continued)

capturing a fundus image, and determining a photography focal length by using the fundus image, and photographing a fundus image by using the photography focal length on the working distance.

9 Claims, 13 Drawing Sheets

(58) Field of Classification Search
USPC .......................................................... 351/208
See application file for complete search history.

(56) References Cited

FOREIGN PATENT DOCUMENTS

| | | | | | |
|----|-------------|---|---|---------|----------------|
| CN | 108346149 | A | | 7/2018 | |
| CN | 208156413 | U | * | 11/2018 | |
| CN | 109547677 | A | | 3/2019 | |
| CN | 111134616 | A | | 5/2020 | |
| CN | 111449620 | A | * | 7/2020 | .......... G06V 40/193 |
| CN | 112043236 | A | | 12/2020 | |
| EP | 2 090 224 | A1 | | 8/2009 | |
| JP | H07-136119 | A | | 5/1995 | |
| JP | 2003217143 | A | * | 7/2003 | |
| JP | 2005-278842 | A | | 10/2005 | |
| JP | 2019042305 | A | * | 3/2019 | |
| JP | 2020-156555 | A | | 10/2020 | |
| WO | WO 2016/111379 | A1 | | 7/2016 | |

OTHER PUBLICATIONS

Office action issued on Mar. 22, 2021 from China Patent Office in a counterpart China Patent Application No. 202011095133.3 (all the cited references are listed in this IDS.) (English translation is also submitted herewith.).

European Search Report For EP21878859.4 issued on Jul. 31, 2024 from European patent office in a counterpart European patent application.

Office action issued on Apr. 2, 2024 from Japan Intellectual Property Office in a counterpart Japanese Patent Application No. 2023-519780 (all the cited references are listed in this IDS.) (English translation is also submitted herewith.).

\* cited by examiner

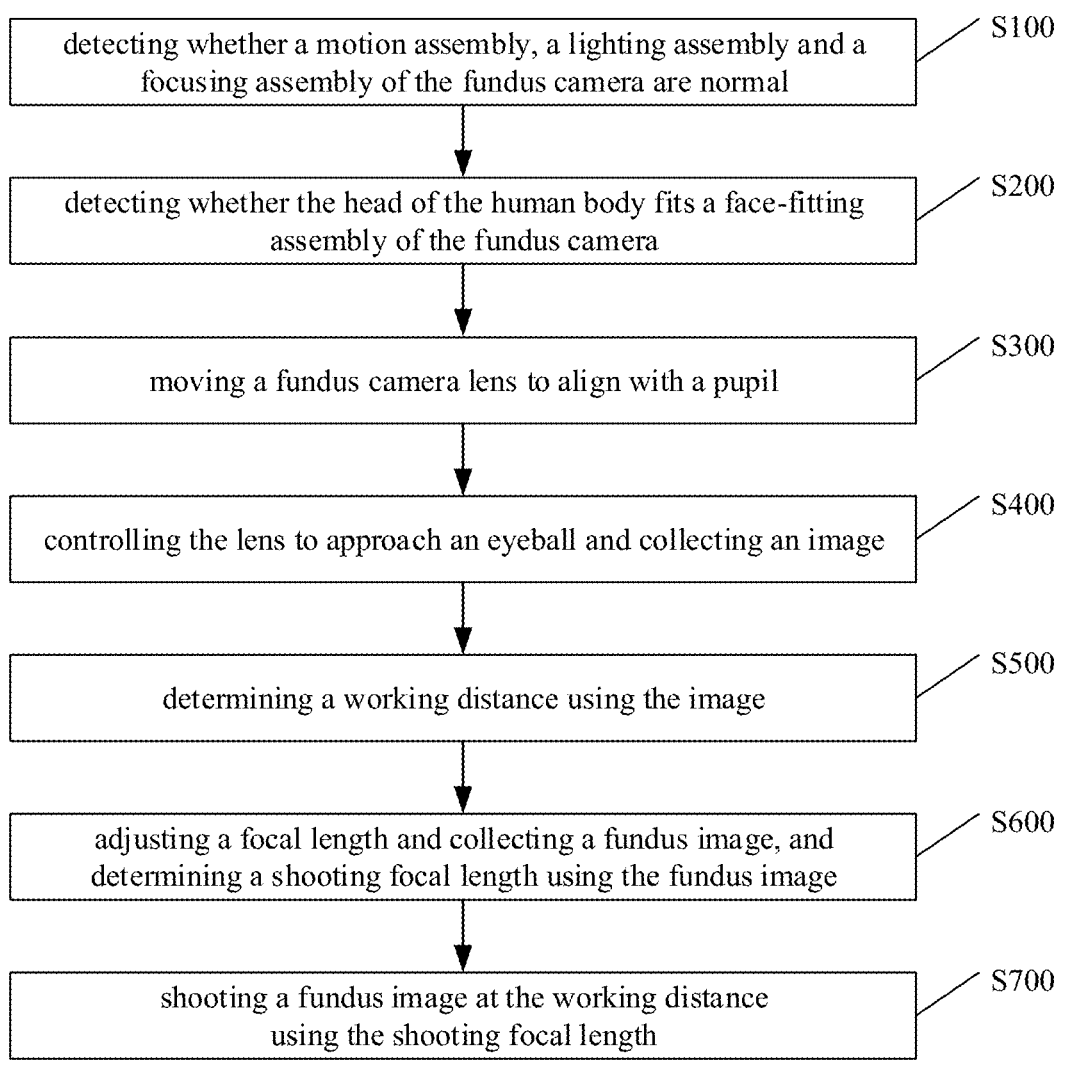

detecting whether a motion assembly, a lighting assembly and a focusing assembly of the fundus camera are normal          S100 detecting whether the head of the human body fits a face-fitting assembly of the fundus camera          S200 moving a fundus camera lens to align with a pupil          S300 controlling the lens to approach an eyeball and collecting an image          S400 determining a working distance using the image          S500 adjusting a focal length and collecting a fundus image, and determining a shooting focal length using the fundus image          S600 shooting a fundus image at the working distance using the shooting focal length          S700

FIG. 6

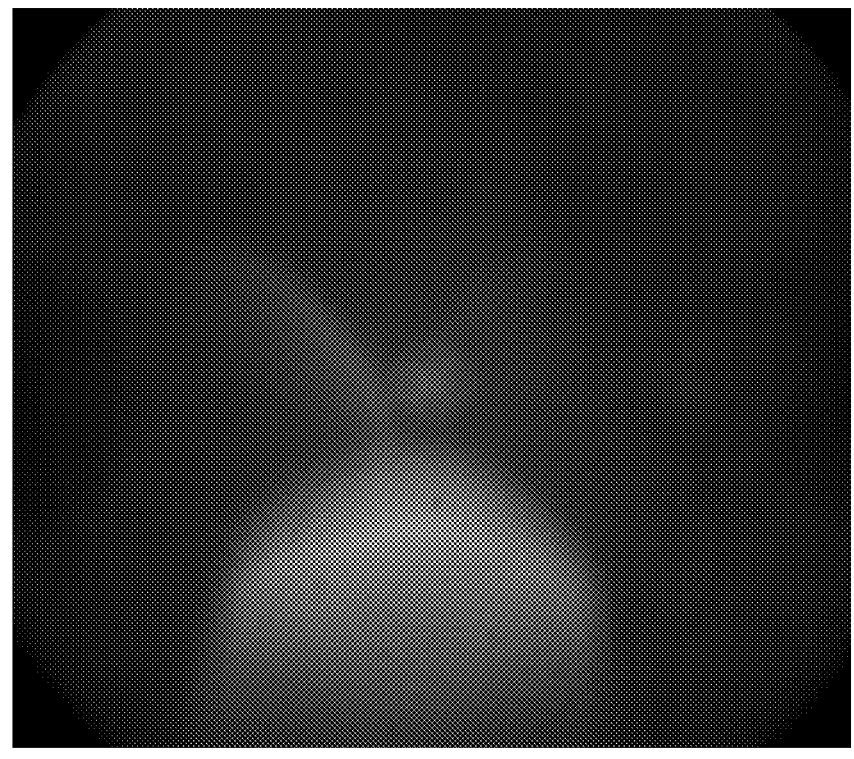
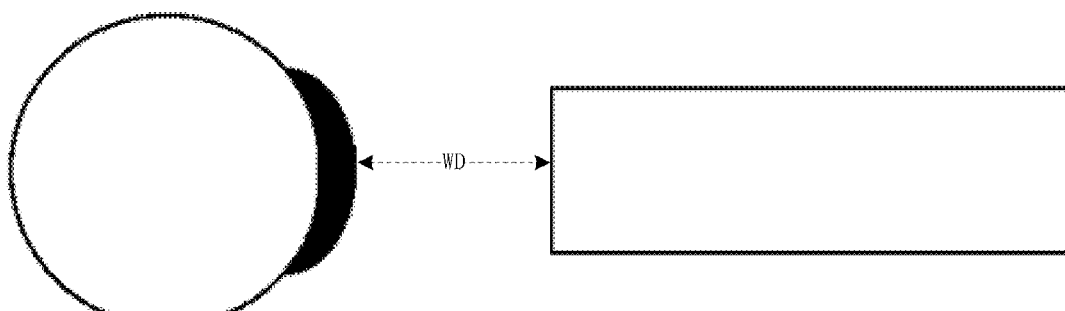
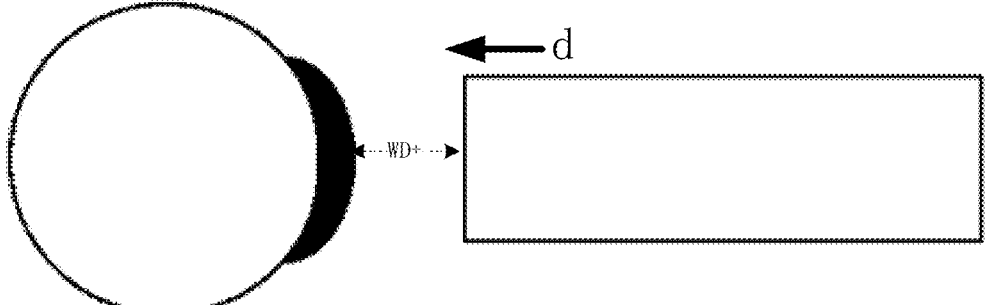
FIG. 13

1

FUNDUS CAMERA AND FULLY-AUTOMATIC PHOTOGRAPHY METHOD FOR FUNDUS IMAGE

CROSS REFERENCE TO RELATED APPLICATIONS AND CLAIM OF PRIORITY

This application claims benefit under 35 U.S.C. 119, 120, 121, or 365(c), and is a National Stage entry from International Application No. PCT/CN2021/073875 filed on Jan. 27, 2021, which claims priority to the benefit of Chinese Patent Application No. 202011095133.3 filed in the Chinese Intellectual Property Office on Oct. 14, 2020, the entire contents of which are incorporated herein by reference.

BACKGROUND

1. Technical Field

The present invention relates to the field of ophthalmic instruments, and in particular, to a fundus camera and a fully-automatic photography method for a fundus camera.

2. Background Art

The retina is the only tissue in which capillaries and nerves can be directly observed in the human body. By observing the retina, not only health problems of the eye can be detected but also systemic diseases such as diabetic complications and hypertension can be discovered. The fundus camera is a dedicated device used to take photos of the retina.

The existing fundus camera can automatically shoot fundus images, and the automatic shooting process mainly relates to automatic alignment of a main lens with pupils, automatic adjustment of an axial distance (working distance) between the lens and the pupils, and automatic adjustment of the focal length. The camera is equipped with a main camera, an auxiliary camera and a plurality of auxiliary optical devices, wherein the main camera is installed on a platform that is movable in three directions of X, Y, Z and is used for shooting the fundus; the auxiliary camera is installed near the main camera and is used for shooting a face and the outer eye and is mainly used for searching the eye and realizing automatic alignment of the pupils; and the auxiliary optical devices are used for focusing, adjusting the working distance, etc.

The existing fundus camera requires complex and expensive hardware modules to solve the problems of aligning the lens with the pupils, fixing the axial distance between the lens and the pupils, and focusing, and it is also complex to use, thereby hindering popularization of the fundus camera.

SUMMARY

In view of the above, the present invention provides a fully-automatic photography method for a fundus image, including:

moving a fundus camera lens to align with a pupil;

controlling the lens to approach an eyeball and acquiring an image, wherein the image is an image of an illuminating light beam reflected by a cornea;

determining a working distance using the image;

adjusting a focal distance and collecting a fundus image, and determining a shooting focal distance using the fundus image; and

shooting a fundus image at the working distance using the shooting focal distance.

Optionally, before moving the fundus camera lens to align with the pupil, the method further includes: detecting whether a motion assembly, a lighting assembly and a focusing assembly of the fundus camera are normal.

Optionally, detecting whether the motion assembly, the lighting assembly, and the focusing assembly of the fundus camera are normal specifically includes:

controlling the motion assembly to adjust the position of the lens, and detecting whether the lens can move to a position of each positioning assembly;

after the lens can be moved to the position of each positioning assembly, controlling the motion assembly to move the lens to a set position, turning on the lighting assembly and controlling the focusing assembly to be adjusted to a first focal length, and shooting to obtain a first image;

determining whether the focusing assembly and the lighting assembly are normal according to image features of the lighting assembly in the first image;

when the focusing assembly and the lighting assembly are normal, controlling the motion assembly to adjust the lens to a set depth position, controlling the focusing assembly to be adjusted to a second focal length, and capturing a second image; and determining whether the imaging function is normal according to the image features of a subject in the second image.

Optionally, before moving the fundus camera lens to align with the pupil, the method further includes: detecting whether a head of a human body fits a face-fitting assembly of the fundus camera.

Optionally, detecting whether the head of the human body fits a face-fitting assembly of the fundus camera specifically includes:

turning off the lighting assembly, and acquiring a first image collected by the lens through a window of the face-fitting assembly;

determining whether the brightness of the first image achieves a set criterion;

when the brightness of the first image achieves the set criterion, turning on the lighting assembly, and acquiring a second image collected by the lens through the window of the face-fitting assembly; and determining whether the head of the human body fits the face-fitting assembly according to the second image.

Optionally, determining the working distance using the image specifically includes:

detecting whether features of a light spot in the image meet set features; and when the features of the light spot meet the set features, determining that the working distance is reached.

Optionally, determining a shooting focal distance using the fundus image specifically includes:

recognizing an optic disc region in the fundus image; and determining a shooting focal distance according to a resolution of the optic disc region.

Optionally, shooting a fundus image at the working distance using the shooting focal distance specifically includes:

determining whether a size of the pupil is smaller than a size of an annular illumination beam of the lighting assembly of the fundus camera;

when the size of the pupil is smaller than the size of the annular illumination beam, moving the lens to multiple directions respectively to generate an offset from the pupil, so that the annular illumination beam is irradiated partially into the pupil, and a plurality of fundus images are shot; and fusing the plurality of fundus images into one fundus image.

Optionally, shooting a fundus image at the working distance using the shooting focal distance specifically includes:

acquiring a plurality of fundus images shot under the condition that the lens state is not changed;

extracting high-quality regions in the plurality of fundus images, respectively; and synthesizing a fundus image using the plurality of high-quality regions.

Accordingly, the present invention provides an electronic device, including: at least one processor; and a memory communicatively coupled to the at least one processor; wherein the memory stores instructions executable by the processor, the instructions, when executed by the at least one processor, causing the at least one processor to carry out the fully-automatic photography method for a fundus image.

Accordingly, the present invention provides a fundus camera, including: a face-fitting assembly, a motion assembly, a focusing assembly, a lighting assembly, a lens and at least one processor; and a memory communicatively coupled to the at least one processor; wherein the memory stores instructions executable by the processor, the instructions when executed by the at least one processor, causing the at least one processor to carry out the fully-automatic photography method for a fundus image.

According to the fundus camera and the fully-automatic photography method for a fundus image provided by the present invention, the fundus camera is able to automatically align the lens with the pupil, automatically adjust the working distance, and automatically adjust the focus length. According to the solution, by an image identification algorithm, the fundus camera can shoot a fundus image fully automatically, without any auxiliary lens or auxiliary optical devices, thereby reducing complexity of the hardware and difficulty in use, enabling a user to autonomously capture a fundus image, and promoting population of the fundus camera.

BRIEF DESCRIPTION OF THE DRAWINGS

In order to more clearly illustrate the embodiments of the present invention or the technical solutions in the prior art, the drawings used in the embodiments or the prior art descriptions will be briefly described below. Apparently, the drawings in the following description are some embodiments of the present invention, and other drawings can be obtained from the drawings by those ordinary skilled in the art without spending any creative efforts.

FIG. 6 is a flowchart of a preferred fully-automatic photography method for a fundus image according to an embodiment of the present invention;

FIG. 13 shows imaging of an illumination beam reflected by the cornea when the working distance is achieved;

DETAILED DESCRIPTION

Figure 1:
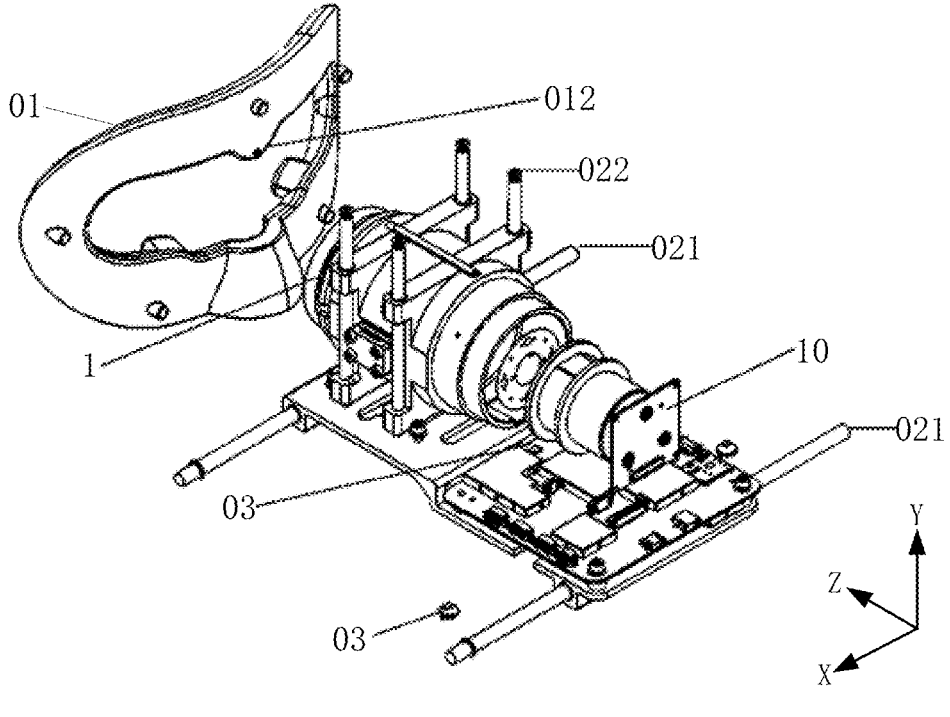
FIG. 1 is a structure diagram of a fundus camera according to an embodiment of the present invention.

The technical solutions of the present invention will be described clearly and completely with reference to the accompanying drawings. Obviously, the described embodiments are only a part, instead of all of the embodiments of the present invention. All other embodiments, which can be obtained by those of ordinary skilled in the art without expending any creative effort based on the embodiments of the present invention, belong to the protection scope of the present invention.

In the description of the present invention, it should be noted that orientations or positional relationships indicated by the terms "center," "upper," "lower," "left," "right," "vertical," "horizontal," "inner," "outer," etc. are orientations or positional relationships shown in the drawings, and the terms are used only for ease of description of the present invention and for simplification of the description, but do not indicate or suggest that the device or element referred to must have a specific orientation, or be constructed and operated in a specific orientation. Thus, the terms should not be construed as limiting the present invention. Furthermore, the terms "first," "second," and "third" are only used for descriptive purposes and are not to be construed as indicating or suggesting relative importance.

In the description of the present invention, it should be noted that, unless otherwise explicitly specified or limited, the terms such as "mounted" "interconnected" and "connected" are to be construed broadly and can be, for example, a fixed connection, a detachable connection, or an integral connection; or can be a mechanical or electrical connection; or can be a direct connection or an indirect connection through an intermediate medium, or a communication of the inside of two elements; or can be a wireless connection or a wired connection. The specific meanings of the above terms in the present invention can be understood in a specific case for those of ordinary skill in the art.

Furthermore, the technical features involved in the different embodiments of the present invention described below can be combined with each other as long as they do not conflict with each other.

FIG. 1 depicts a fully-automatic portable self-photographing fundus camera, which includes a face-fitting assembly 01, a motion assembly, a positioning assembly 03 and a lens barrel 1, wherein a lighting assembly, a focusing assembly, a lens (an eye-contacting objective lens), an optical lens group, an imaging detector 10, and the like are provided inside the lens barrel 1, and the internal structure of the lens barrel 1 can refer to the Chinese patent document No. CN111134616A. An actual product also includes a housing inside which the motion assembly and the lens barrel 1 are located. The face-fitting assembly 01 is connected to a front part of the housing in a sealing mode, the face-fitting assembly 01 including a face-fitting body, and a window through hole formed on the face-fitting body and used for accommodating the eye when the eye of the subject fits the face-fitting assembly 01. The face-fitting assembly 01 serves as a part contacting the eyes of the subject, and the lens barrel 1 collects a fundus retinal image of the subject through the through hole of the face-fitting assembly 01.

Figure 2:
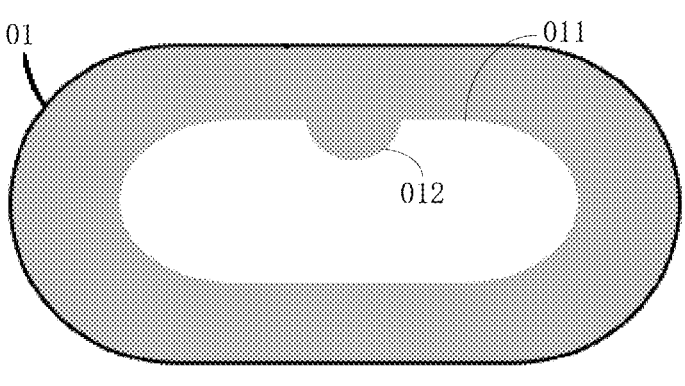
FIG. 2 is a schematic diagram of a face-fitting assembly of the fundus camera according to an embodiment of the present invention.

A face of the face-fitting body facing away from the lens barrel 1 is configured into a shape that fits a facial contour around the eye of the subject. Specifically, the face-fitting assembly 01 is inwardly formed into a concave shape to fit the arc shape of the head of a human body, and a size of the through hole of the face-fitting assembly 01 is at least capable of accommodating eyes when the eye of the subject fits the assembly. A face of the face-fitting assembly 01 facing inwards (within the housing and the lens barrel 1) has at least one specific position for detecting various functions of the camera. In a specific embodiment, with reference to FIGS. 1 and 2, FIG. 2 depicts a face of the face-fitting assembly 01 that faces inwardly, a protrusion 012 is provided at an upper edge of a middle portion of a through hole 011, and a lens of the lens barrel 1 can be aligned with the protrusion 012 and take an image thereof. More preferably, a pattern or a simple figure is provided on the protrusion 012 as a target. The specific position has multiple functions, including detecting whether the lighting assembly and the focusing assembly of the camera are normal, detecting whether the eye of the subject correctly fits the face-fitting assembly 01 and the like, which will be described in detail below.

The motion assembly is used for controlling the lens barrel 1 to move in a three-dimensional space, for example, in a coordinate system as shown in FIG. 1, the lens barrel 1 can move along three axes, i.e., X, Y, and Z axes. It should be noted that when the lens barrel 1 moves to a limit position in the Z direction, its end portion would not protrude outside the face-fitting assembly 01. In a specific embodiment, the motion assembly includes three rail components, wherein a first set of rails 021 is used for controlling movement of the lens barrel 1 along the X axis, a second set of rails 022 is used for controlling movement of the lens barrel 1 along the Y axis, and a third set of rails that is not shown in the figure is used for controlling movement of the lens barrel 1 along the Z axis. Specifically, the lens barrel 1 is disposed on a platform (base) together with the second set of rails 022, and the first set of rails 021 can drive the base to move integrally, and the third set of rails can drive the base and the first set of rails 021 to move, such that the entirety approaches or leaves the face-fitting assembly 01.

Figure 3:
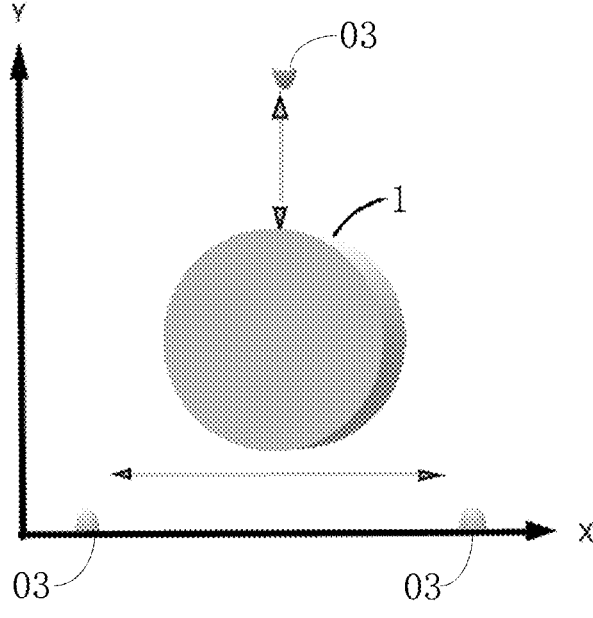
FIG. 3 is a schematic diagram of a lens and a positioning assembly.

The positioning assembly 03 is used for detecting movement of the lens barrel 1. Specifically, the positioning assembly 03 can be an electromagnetic sensor, which senses that the lens barrel 1 moves to a position of the positioning assembly 03 according to an electromagnetic induction signal. In an embodiment as shown in FIG. 3, three positioning assemblies 03 are provided, two of which are disposed on two sides of a movable base to detect movement of the lens barrel 1 along the X axis, and a third of which is disposed on the base to detect movement of the lens barrel 1 along the Y axis, i.e., the positioning assembly 03 is used for detecting movement of the lens barrel 1 in an XY plane.

According to the fundus camera provided by the invention, the lighting assembly, the focusing assembly, the eye-contacting objective lens, the optical lens group and the imaging detector which are used for imaging are integrated in one lens barrel in order to miniaturize the optical path structure, reduce volume of the fundus camera and improve portability of the camera; the face-fitting assembly of the fundus camera is provided with the window through-hole that is used for holding the eye of the subject, and the user can wear the fundus camera by himself/herself and arrange the eye at a position of the window through-hole; the motion assembly drives the lens barrel to search for the pupil in the range of the window through hole and adjusts the working distance, thereby shooting the fundus image. This solution has reduced complexity and difficulty in use of the fundus camera hardware, enables a user to independently shoot the fundus image, and promotes popularization of the fundus camera.

Figure 4:
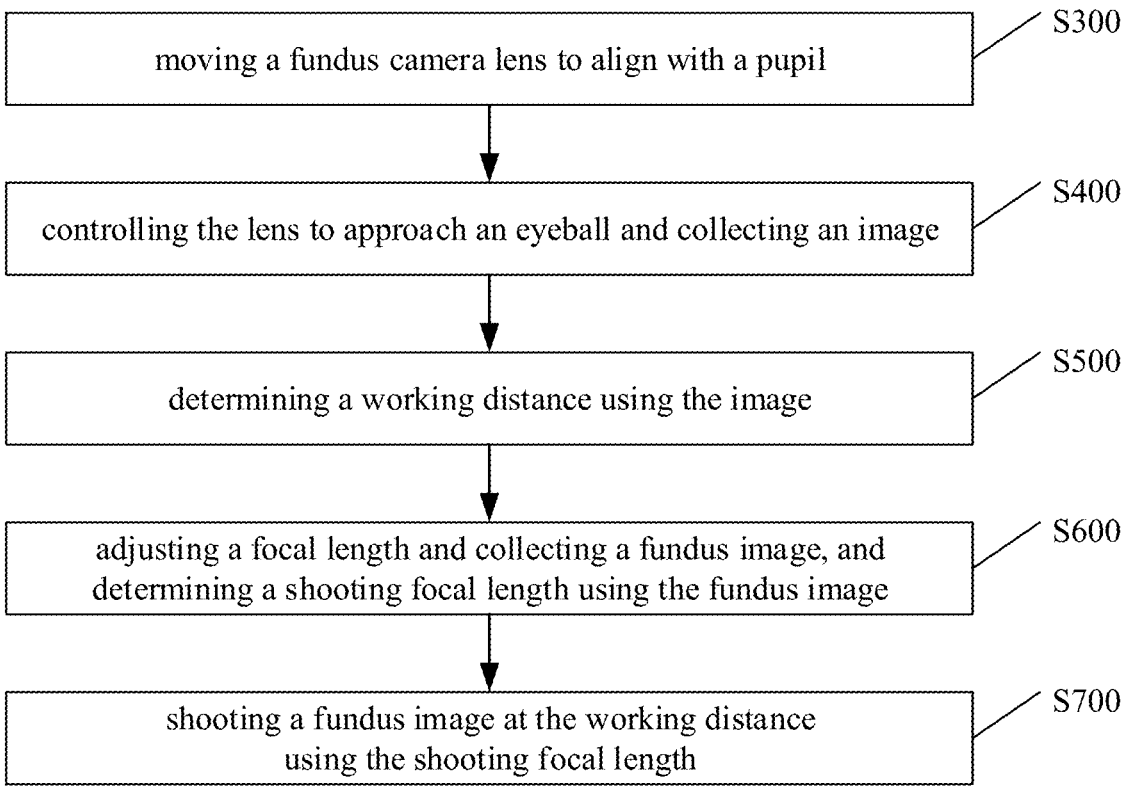
FIG. 4 is a flowchart of a fully-automatic photography method for a fundus image according to an embodiment of the present invention.

The embodiments of the present invention provide a method for fully-automatic photography of fundus images, which can be performed by the fundus camera itself or by an electronic device such as a computer or a server (as a control method). As shown in FIG. 4, the method includes the following steps:

S300, moving a fundus camera lens to align with a pupil.

S400, controlling the lens to approach an eyeball and collecting an image, wherein the image is an image of an illumination beam reflected by the cornea.

S500, determining a working distance using the image.

S600, adjusting a focal length and collecting a fundus image, and determining a shooting focal length using the fundus image.

S700, shooting a fundus image at the working distance using the shooting focal length.

In a preferred embodiment, prior to the step S100, a step of detecting a camera status and a user usage status can be further performed, and as shown in FIG. 6, the method can further include:

S100, detecting whether a motion assembly, a lighting assembly and a focusing assembly of the fundus camera are normal. As an optional operation, this step can be performed at the time of powering on the fundus camera. If it is detected that a certain component is abnormal, the subsequent shooting operation is terminated and a corresponding abnormality alarm is given.

S200, detecting whether the head of the human body fits a face-fitting assembly of the fundus camera. As an optional operation, the user can be prompted by a voice module if it is detected that the human head does not fit the face-fitting assembly of the fundus camera to guide the user to correctly wear the fundus camera.

In view of the above step S100, an embodiment of the present invention provides a fundus camera detection method which can be performed by a fundus camera itself as a self-inspection method, or can be performed by an electronic device such as a computer or a server as a product detection method, the method including the following steps:

S1, controlling the motion assembly to adjust a position of the lens, and detecting whether the lens can move to a position of each positioning assembly. The method is adapted to be carried out when the fundus camera has just been powered on. Firstly, the lens (according to the above-described embodiment, the lens and the lens barrel are provided integrally, and movement of the lens barrel means movement of the lens) is moved to an initial position. Then, as shown in FIG. 3, the motion assembly adjusts the position of the lens, and detects whether the lens can move to positions of the three positioning assemblies. If movement to these positions is possible, then it is deemed that the motion assemblies function normally and step S2 can be executed; otherwise, step S6 is executed. Step S1 can be referred to as a motion detection step of the motion assembly along the XY axes.

S2, controlling the motion assembly to move the lens to a set position, turning on the lighting assembly and controlling the focusing assembly to adjust to a first focal length, and shooting to obtain a first image. The purpose of this step is to detect whether the focusing assembly and the lighting assembly are functioning normally. Theoretically, it is not necessary to limit that the lens must be aligned to a certain position, and therefore, there are multiple choices for the set position in this step. However, in an actual working environment, an external environment is uncertain, which can be, for example, a relatively bright environment, and if the external environment is relatively bright when the first image is captured in this step, the image content can be disturbed. In order to adapt to the actual working environment, in this step, the lens is moved to a certain specific part (such as the protrusion described above) of the face-fitting assembly, such that the external environment is shot as little as possible, and an occupation ratio of the face-fitting assembly in the image is larger than that of the external environment. Of course, it is also possible to modify the shapes of the face-fitting assembly and its through-hole so that the image taken at this step contains no external environment at all.

Figure 18:
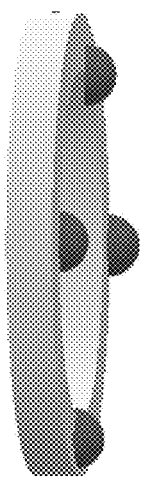
FIG. 18 is a structure diagram of a lighting lamp.
Figure 19:
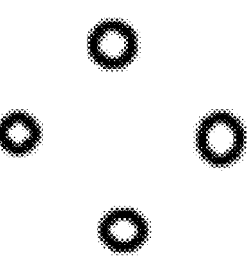
FIG. 19 is a schematic diagram of imaging illumination reflected light when a camera status is detected.

By setting an appropriate focal length, the lighting assembly can be imaged. For example, FIG. 18 shows the structure of a lighting lamp in one lens barrel, with four lamp beads arranged on one annular structure. The four lamp beads are turned on, and the first focal length is used for imaging, in an expectation to obtain an image as shown in FIG. 19.

In a preferred embodiment, in order to avoid the influence of the background on imaging of the lighting assembly in a captured image, the first focal length is set to enable imaging of the lighting assembly but not of the face-fitting assembly. Accordingly, the first image can include only the lighting assembly but not objects such as the protrusion of the face-fitting assembly and the like, thereby enhancing accuracy of image recognition in the subsequent steps.

S3, determining whether the focusing assembly and the lighting assembly are normal or not according to image features of the lighting assembly in the first image. In a case where the focusing assembly functions normally, the use of the set focal length would result in an image as shown in FIG. 19, the image has distinct features that are specifically dependent on the actual shape of the lighting assembly. For example, in this embodiment, the first image should include four independent and clear dots, which results from imaging of the four lamp beads. If the adjusted focal length at this time is not the first focal length, the dots in the image will become larger and blurred, or become smaller; if the lighting assembly is not turned on, no shape will appear in the image.

The first image is recognized through a machine vision algorithm or a neural network algorithm, both of which can recognize whether the image includes feature satisfying the expectation. If it is determined that the focusing assembly and the lighting assembly are normal, step S4 is performed; otherwise, step S6 is performed. Steps S2-S3 can be referred to as focusing assembly and lighting assembly detection steps.

S4, controlling the motion assembly to adjust the lens to a set depth position, controlling the focusing assembly to adjust to a second focal length, and shooting to obtain a second image. In this step, it is necessary to image a known object, and as a preferred embodiment, the protrusion of the face-fitting assembly is used as the known object. Specifically, the lens is first aligned with the protrusion of the face-fitting assembly on the XY plane, and in this embodiment, this part has been aligned in step S2, which does not need to be adjusted in this step; in other embodiments, if this part is not aligned in step S2, an adjustment is made in this step. This step requires adjusting the depth, i.e., adjusting the position of the lens on the Z-axis which can be understood as adjusting a shooting distance to a known object, and then setting the focal length.

Figure 20:
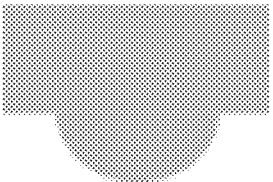
FIG. 20 is a schematic diagram of imaging of a protrusion of a face-fitting assembly when a camera status is detected.

In order to enable imaging of an external object, the focal length at this time is different from the focal length used in step S2, and the focal length in this step should be adapted to the current lens position (depth position), in an expectation to obtain an image as shown in FIG. 20.

In a preferred embodiment, in order to avoid an influence of an image of the lighting assembly on the imaging of the subject in the captured image, the second focal length is set to enable imaging of the face-fitting assembly but not of the lighting assembly. Accordingly, the second image can include only the subject, such as the protrusion of the face-fitting assembly, but no image of the lighting assembly, thereby enhancing accuracy of image recognition in the subsequent steps.

S5, determining whether the imaging function is normal or not according to the image features of the subject in the second image. The second image is an image captured in a case where both movement of the motion assembly on the XY axes and the lighting assembly and the focusing assembly are normal. The purpose of this step is to detect whether the movement of the motion assembly on the Z axis is normal. If the motion assembly can adjust the lens to the set depth position in step S4, a clear subject, such as the protrusion of the face-fitting assembly as shown in FIG. 20, should be displayed in the captured second image.

The second image is recognized through the machine vision algorithm or the neural network algorithm, both of which can recognize whether expected features exist in the image. If it is determined that movement of the motion assembly on the Z axis is normal, the detection is terminated, and it is determined that functions of the respective main components of the fundus camera are normal; otherwise step S6 is executed. Steps S4-S5 can be referred to as a motion detection step of the motion assembly along the Z-axis.

S6, determining a state of the fundus camera is abnormal. The user is prompted with a specific failed part according to the abnormal component. A voice module or an information display module can be arranged in the fundus camera to broadcast or display corresponding failure information to the user.

A fundus camera detection method provided according to the embodiment of the invention include the following steps:

verifying, by a positioning assembly, whether the motion assembly can normally adjust the position of the lens; after confirming the motion assembly is normal, adjusting the focal length to enable the lighting assembly to image, and determining the acquired image to determine whether the focusing assembly and the lighting assembly are normal; finally, adjusting a depth of the lens through the motion assembly, adjusting the focal length to image the subject, and determining the features of the object in the image, to verify whether the motion assembly can normally adjust the depth of the lens, so that it is automatically determined whether each important part of the fundus camera can operate normally. This solution can be used for carrying out self-service inspection on the working state of a device in a remote unattended environment, thereby enhancing convenience of shooting the fundus photo and promoting popularization of the fundus camera.

Figure 21:
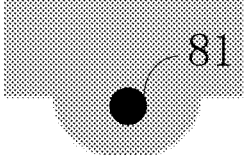
FIG. 21 is a schematic diagram of imaging of a protrusion of a face-fitting assembly with a target when a camera status is detected.

In a preferred embodiment, a target is provided on the protrusion of the face-fitting assembly, i.e., the above-mentioned subject is a target on a set part of the face-fitting assembly. The specific content of the target is not limited, which can be one or more patterns or shapes with clear profile. The resulting second image is shown in FIG. 21, which includes a circular target 81. The step S5 specifically includes:

S51, recognizing whether a clear target image exists in the second image; and S52, determining that the imaging function is normal when a clear target image exists in the second image.

Target recognition by using the machine vision algorithm or the neural network algorithm would have a more accurate result. If a target does not exist in the image or the target has an unclear profile, the recognition would be easier, so that the accuracy of camera function judgment is further improved.

In relation to said step S200, an embodiment of the present invention provides a fundus camera use state detection method for detecting whether the user has correctly worn the fundus camera in the embodiment. The method can be executed by the fundus camera itself as a self-inspection method, or can be executed by an electronic device, such as a computer or a server. The method is suitable for being executed after determining the important parts of the camera are normal according to the detection method, and includes the following steps:

S1, acquiring a first image collected by the lens through the window of the face-fitting assembly. In this solution, the lens collects an image of an external environment through the through hole 011 shown in FIG. 2. It should be avoided that the face-fitting assembly blocks the lens (the face-fitting assembly is not in an imaging range). When the subject correctly wears the fundus camera, his/her eye fits the face-fitting assembly 01. The two eyes of the human body and surrounding skin are within the window (the through hole 011), and the lens collects a corresponding first image. During this step, it is necessary to keep the lighting assembly in a closed state, i.e., no light beam is irradiated outward through the lens. In this solution, since there is no high requirement on resolution of the collected image, the focal length used for collecting the image can be a fixed value, and the imaging plane is approximately arranged on the surface of the human body. Of course, the lighting assembly can be turned on first to perform automatic focusing, and after the imaging plane is set more accurately on the surface of the human body, the lighting assembly can be turned off.

S2, determining whether brightness of the first image reaches a set criterion If the eye of the subject fits the face-fitting assembly without large gaps around the eyes, the collected first image should be very dark. The brightness of the first image is determined firstly, and step S3 is performed if the brightness reaches the set criterion; otherwise, step S6 is performed.

There are various methods for determining whether the brightness of the image meets the set criterion, including, for example, calculating a brightness value according to a pixel value of the image, and then comparing the brightness value with a threshold value; alternatively, a neural network algorithm can be employed, including training a neural network in advance by using images with different brightness, so that the neural network has the capability of classification or regression prediction of the image brightness, and the neural network is used to recognize the first image and output the recognition result about the brightness.

In a preferred embodiment, the first image is converted into a grayscale image and then brightness of the grayscale image is recognized.

Figure 22:
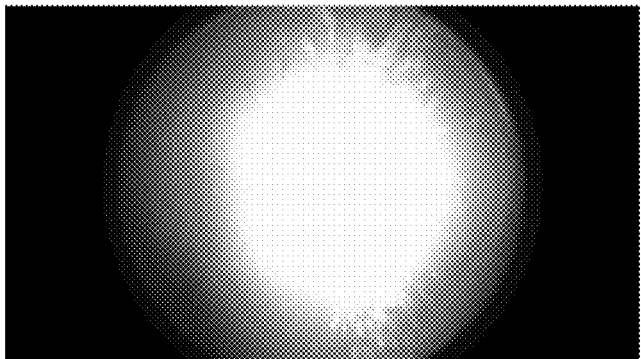
FIG. 22 is an image of an area between both eyes acquired when a usage state of the subject is detected.

S3, turning on the lighting assembly to obtain a second image collected by the lens through the window of the face-fitting assembly. At this time, the states of the lens and the subject are not changed, only an illumination light source being turned on for illumination outwardly through the lens. At this time, the illumination beam irradiates the eyes or the skin of the subject and is reflected. In a preferred embodiment, the lens is positioned to be aligned with a center position of the window of the face-fitting assembly, and the light source used is infrared light. If the head of the human body fits the face-fitting assembly, the lens is aligned with an area between the eyes, and an image as shown in FIG. 22 can be acquired.

S4, determining whether the head of the human body fits the face-fitting assembly or not according to the second image. If the head of the subject fits the face-fitting assembly, due to reflection of an illumination beam by the human skin, an obvious light spot would appear in an image shown in FIG. 22, and human skin features would be presented in the periphery of the light spot. It is determined whether the head of the human body fits the face-fitting assembly by determining whether the image has features of a bright center and gradually darker edges.

Assuming that no object fits the face-fitting assembly in steps S1-S2, and the camera is placed in a dark room, or the face-fitting assembly is covered by another object, the brightness of the first image will also be determined to meet the set criterion, which requires further execution of steps S3-S4 for determination. If no object fits the face-fitting assembly, no light spot would appear in the acquired second image; if another object covers the face-fitting assembly, light spots would appear in the second image. However, because of differences in material and surface shape, the reflection condition of the illuminating light beams is different from that of a human body, and therefore it can be determined whether it is a human body or not through features of the light spots.

In another alternative embodiment, the lens can be aligned at other positions when the first and second images are acquired, such as aligning with the eyeball, and in step S4, the eyeball feature can be recognized in the image to determine whether the image is a human body.

In a preferred embodiment, step S4 can include first determining whether brightness of the second image meets a set criterion, and similar to recognizing the brightness of the first image, the second image can be converted into a grayscale image and then its brightness value is calculated, or the recognition can be performed using a neural network.

If a gap appears at the joint of the face-fitting assembly and the human body at the moment, which leads to light leakages, the brightness of the second image, affected by ambient light, is different from the brightness when only the light source of the camera itself is used for illumination. With exclusion of light leakage, it is determined whether features in the second image satisfy features of human skin.

Step S5 is performed when it is determined the human head fits the face-fitting assembly; otherwise, step S6 is performed.

S5, starting to shoot a fundus image. Specifically, it needs to automatically seek for the pupil, adjust a working distance, adjust a focal length to provide an imaging plane on the fundus, and finally obtain a fundus image by shooting.

S6, prompting the user to correctly wear the fundus camera. For example, a voice module can be provided in the fundus camera, prompting the user how to correctly wear the fundus camera, and the like, and then, the process can return to step S1 for re-judgment.

A method for detecting the use state of the fundus camera provided according to the embodiment of the invention, including acquiring an image under the condition that the lighting assembly is turned off, preliminarily determining whether the face-fitting assembly is well covered by an object according to the brightness of the image, and then acquiring an image under the condition that the lighting assembly is turned on, and determining whether the covering object is a human body according to the image features, so that it can be automatically determined whether the subject has correctly worn the fundus camera and whether the subject uses the fundus camera in a proper environment. This solution can automatically trigger the fundus camera to shoot fundus photos, without manual intervene for triggering and shooting, and no professional personnel is required for operation, thereby improving convenience of shooting fundus photos and promoting popularization of the fundus camera.

When a camera starts to shoot, the pupil and the eye-contacting objective lens are not completely aligned with each other in an actual application scene, and at the moment, the camera is required to judge a position of the lens relative to the pupil through imaging of the pupil on a sensor, and then the lens is moved to a position right in front of the pupil for shooting. In view of said step S300, an embodiment of the present invention provides a method for automatic alignment of a lens of a fundus camera, which can be executed by the fundus camera itself or can be executed by an electronic device such as a computer or a server (as a control method), and the method includes the following steps:

S1, recognizing an image collected by the lens of the fundus camera, and determining whether a pupil exists in the image. Specifically, after a user wears the fundus camera, the system would continuously (for example, frame by frame) acquire images of the pupil, and if the pupil can be recognized in an image, it indicates that the pupil has already been within the imaging range, and in this case, fine adjustment is performed to completely align the lens with the pupil for shooting. If the pupil cannot be recognized in an image, it indicates that the lens has a large deviation from the pupil position, which can be caused by an inappropriate initial position of the lens or a non-standard wearing manner by the user.

There are various ways to recognize a pupil image in an image, including, for example, a machine vision algorithm in which the pupil contour and position are detected according to graphic features in the image. However, since the fundus camera is illuminated with infrared light before the final shooting, the pupil is not imaged very clearly, and reflection by the cornea would also bring much difficulty in pupil detection. In this case, the machine vision algorithm would easily result in misjudgment, and a depth learning algorithm is used in a preferred embodiment to solve the problem.

First, a large number of photos of the pupil are taken, these images being taken of different persons at different times and in different directions and distances from the eye-contacting objective lens of the fundus camera. Then, the pupil in each image is labeled, so as to obtain training data for training a neural network. The labeled data are used to train a neural network model (such as a YOLO network), and after training, a recognition result of the neural network model includes a detection box for characterizing position and size of the pupil in the image.

Figure 5:
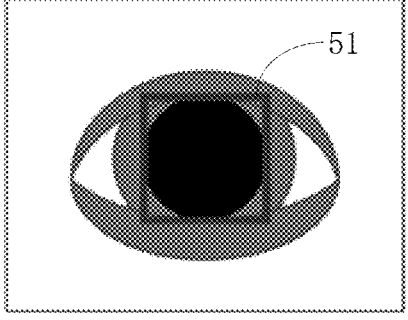
FIG. 5 is a schematic diagram labeling a pupil.

As shown in FIG. 5, in a specific embodiment, a square frame 51 is used in the training data to label the pupil, and the recognition result of the trained neural network model will also be a square detection frame. In other embodiments, a circular box can be used for labeling, or other similar labeling methods can be used.

No matter which pupil detection method is adopted, in this step, it is only necessary to recognize whether a pupil exists in the image, and if no pupil exists in the image, step S2 is executed; otherwise, step S3 is executed.

S2, controlling the fundus camera lens to move in proximity of a current position to search for a pupil. The lens barrel is moved by the motion assembly, in, for example, a spiral track movement, spreading gradually from the current position to the periphery. It should be noted that this embodiment only relates to the movement in the XY plane, and does not discuss movement along the Z axis the movement of the Z axis relates to an optimal working distance of the fundus camera and will be described in detail in the following embodiments.

If the pupil still cannot be searched after movement to a limit position, the user is prompted to adjust the wearing state; if the pupil is searched, it is further determined whether the eye of the user deviates far away from the lens and exceeds a movable range of the motion assembly. For example, it is determined whether a moving distance of the lens exceeds a moving threshold, and when the moving distance exceeds the moving threshold, the user is prompted to slightly move the head within the face-fitting assembly to adapt to the moving range of the lens. Then, the search is continued, and when the moving distance does not exceed the moving threshold, step S3 is performed.

S3, determining whether the pupil in the image meets the set conditions. Specifically, various set conditions can be set, including, for example, a condition regarding a size, a condition regarding a shape, and the like.

In an alternative embodiment, the set condition includes a size threshold. It is determined whether a size of a pupil in the image is greater than the size threshold, and when the size of the pupil in the image is greater than the size threshold, it is determined that a pupil meeting the set condition exists; otherwise, the user is prompted to close the eyes and rest for a period of time, and the shooting is started when the pupil is enlarged. When fundus images are shot, generally, the two eyes are shot in sequence; the pupil can be reduced after a first eye is shot, so the system would also ask the user to close the eyes for rest and restore the pupil size.

In a further alternative embodiment, the setting condition includes a morphological feature. It is determined whether the shape of the pupil in the image meets the set morphological feature. When the shape of the pupil in the image meets the set morphological feature, it is determined that there is a pupil meeting the setting condition; otherwise, the user is prompted to open his/her eyes, not to blink, etc. The set morphological feature is circular or approximately circular. If the detected pupil does not meet the preset morphological feature, for example, the pupil can be flat, which is generally caused by the user' eyes not being open.

In a third alternative embodiment, the neural network model is required to be used for pupil detection, and the recognition result of the neural network model further includes confidence information of pupil, that is, a probability value used for representing the pupil existence in the image determined by the model. The set condition includes a confidence threshold, and it is determined whether confidence information obtained from the neural network model is greater than the confidence threshold. When the confidence information is greater than the confidence threshold, it is determined that a pupil meeting the set condition exists; otherwise, the user is prompted to open his/her eyes and remove shelters such as hair and the like. A confidence of the pupil obtained from the neural network model is relatively low, which indicates that the pupil can be interfered by other objects although a pupil exists in the image. In order to improve the shooting quality, the user is prompted to make an adjustment.

The above three embodiments can be used alternatively or in combination. When the pupil in the image meets the setting condition, step S4 is executed; otherwise, waiting for the user to adjust his/her state and making the judgment until the set condition is met.

S4, moving the fundus camera lens according to a position of the pupil in the image to align the fundus camera lens with the pupil. The lens barrel is moved by the motion assembly, and the moving direction and distance depend on a deviation of the pupil in the image from the lens. A central point of the acquired image is taken as a central point of the lens, and a central point of the pupil in the image is recognized. An example way of recognizing a central point of the pupil in the image is that when a pupil is detected using the neural network model, the central point of the detection frame can be regarded as the center point of the pupil. Step S4 specifically includes:

S41, determining the moving distance and the moving direction according to the deviation between the central position of the detection frame and the central position of the image; and S42, moving the fundus camera lens according to the determined moving distance and moving direction to align the fundus camera lens with the pupil.

A fundus image shooting method is provided according to an embodiment of the invention. The method can include automatically determining whether the current pupil state of the subject is suitable for shooting a fundus image by determining the pupil state in the image; when the state of the subject is not suitable for shooting the fundus image, a corresponding prompt can be sent to the subject to enable the subject to adjust his/her own state, and when the state of the subject is suitable for shooting the fundus image, the pupil position is recognized for automatic alignment, and then shooting is carried out, so that unusable fundus images are prevented from being shot. No professional is required in the whole process, and the user can independently shoot the fundus image.

In practical application scenarios, a particular situation can arise where the size of the pupil can be smaller than the size of the annular illumination beam, in which case the alignment of the pupil with the eye-contacting objective lens would result in no light entering the pupil, and the captured image is therefore dark.

Figure 7:
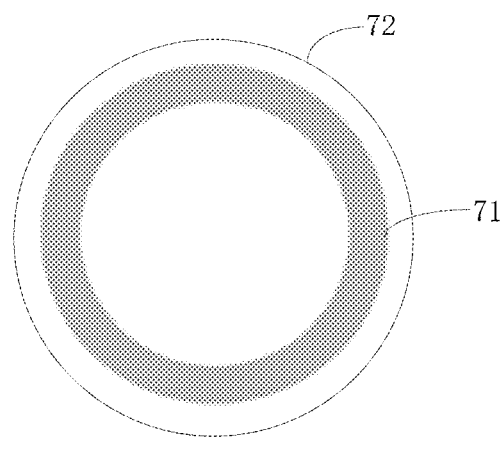
FIG. 7 is a schematic diagram of a pupil being larger than an illumination beam.

In order to solve this problem, with respect to step S700 described above, an embodiment of the present invention provides a preferable fundus image shooting method, including the steps of:

S51, determining whether the size of the pupil in the image is smaller than the annular illumination beam of the lighting assembly of the fundus camera. FIG. 7 shows a case where a pupil 72 has a size larger than the size of an annular beam 71, and in this case, step S52 is performed.

Figure 8:
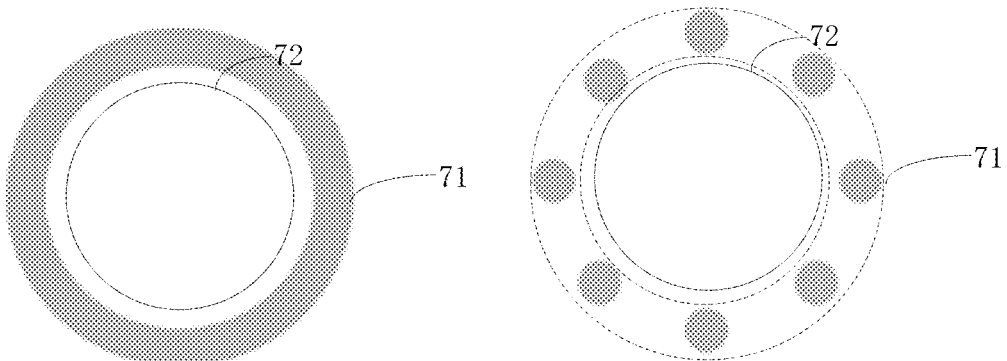
FIG. 8 is a schematic diagram of a pupil being smaller than an illumination beam.

FIG. 8 shows the case where the size of two annular illumination beams is larger than the size of the pupil, wherein the illumination light source is a complete annular illumination lamp or a light source formed by a plurality of illumination lamps arranged in an annular shape, and an inner diameter of the annular beam 71 is larger than a diameter of the pupil 72.

When the size of the pupil is smaller than the size of the annular illumination beam, i.e., as is the case in FIG. 8, step S53 is performed.

S52, shooting a fundus image at a current lens position. This is an image taken when the light source illuminates the fundus of the eye well.

S53, moving the lens to a plurality of directions respectively to deviate it from the pupil, such that the annular illumination beam is irradiated partially into the pupil, and a plurality of fundus images are obtained. Taking the movement shown in FIG. 9 as an example. In this embodiment, the lens is moved respectively in two horizontal directions: when the lens is moved to one side so that a part 73 of the annular beam 71 is irradiated into the pupil 72, one fundus image is taken at this time; when the lens is moved to the other side so that another part 74 of the annular beam 71 is irradiated into the pupil 72, another fundus image is taken at this time.

Figure 9:
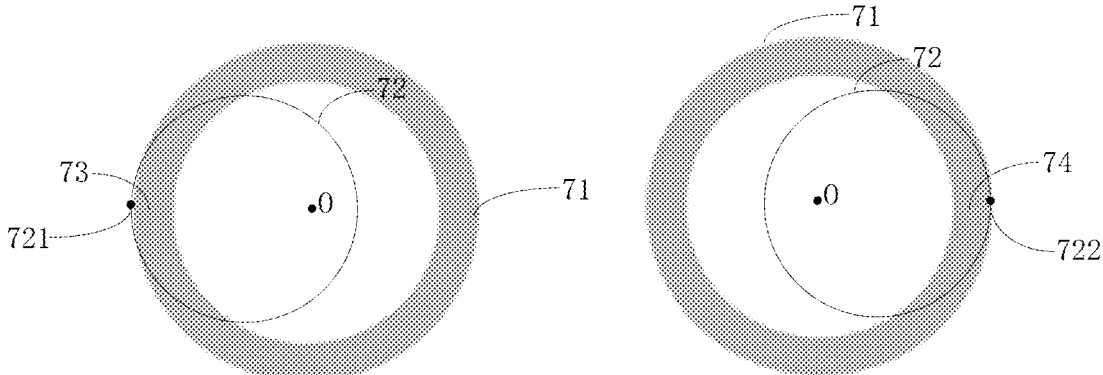
FIG. 9 is a schematic diagram of a fundus image taken with a pupil smaller than an illumination beam.

The movement and illumination shown in FIG. 9 are only examples for illustrating the shooting situation, and in practical applications, the movement can be in more directions so as to shoot more fundus images. However, fundus images shot with such movement and illumination can have overexposure in partial areas, and such fundus images cannot be directly taken as a result of the capturing, and therefore, step S54 is performed.

In addition, to reduce overexposed areas, in a preferred embodiment, movement and shooting are carried out as follows:

S531, determining an edge position of the pupil. Specifically, the machine vision algorithm or the above-mentioned neural network model can be used to obtain a left edge point 721 and a right edge point 722 of the pupil 72 as shown in FIG. 9.

S532, determining a moving distance according to the edge positions of the pupil. Specifically, the moving distance of the motion assembly can be calculated from a positional relationship between a position 0 of the current lens center (a center position of the image) and the left edge point 721 and the right edge point 722.

S533, moving the lens to a plurality of directions respectively according to the determined moving distance, wherein the determined moving distance enables the edge of the annular illumination beam to coincides with the edge position of the pupil. As shown in FIG. 9, an outer rim of the annular beam 71 coincides with a rim of the pupil 72, which makes it possible to locate the portion of the annular beam 71 entering the fundus at the rim of the fundus, thereby reducing the effect on the imaging of the central region of the fundus.

S54, fusing a plurality of fundus images into one fundus image. In this step, usable regions are extracted respectively from the respective fundus images, and a complete fundus image is obtained by splicing and fusing these fundus images. There are various ways for the splicing and fusing, and as an alternative embodiment, step S54 specifically includes:

S541a, calculating displacement deviations of a plurality of fundus images according to the lens moving distance corresponding to the acquired fundus images;

S542a, selecting effective regions in the plurality of fundus images; and

S543a, splicing the effective regions according to the displacement deviation to obtain a spliced fundus image. Further, an image fusing algorithm is used for fusion processing on the splicing positions of each of the effective regions.

As another alternative embodiment, step S54 specifically includes:

S541b, detecting corresponding feature points in the plurality of fundus images;

S542b, calculating a spatial transformation relationship of the plurality of fundus images according to positions of the feature points;

S543b, setting the plurality of fundus images under the same coordinate system according to the spatial transform relationship; and S544b, selecting effective regions for splicing from the plurality of fundus images in the same coordinate system to obtain a spliced fundus image.

A fundus image shooting method is provided by an embodiment of the invention, in which, when the lens of the fundus camera is aligned with the pupil, firstly, a size of the pupil in the image and a size of an annular beam emitted by the camera itself are determined and compared; if the size of the pupil is so small, that the illumination beam cannot normally irradiate the fundus, the lens is moved to deviate from the current alignment position, so that the annular illumination beam is partially irradiated into the pupil, and fundus images at a plurality of deviation positions are obtained, and finally one fundus image is obtained by fusing a plurality of fundus images. According to this solution, a fundus image can be shot when the pupil of the subject has a small size, and no professional is required to participate in the shooting process, thereby reducing requirement on the pupil state of the subject and increasing the shooting efficiency.

Figure 10:
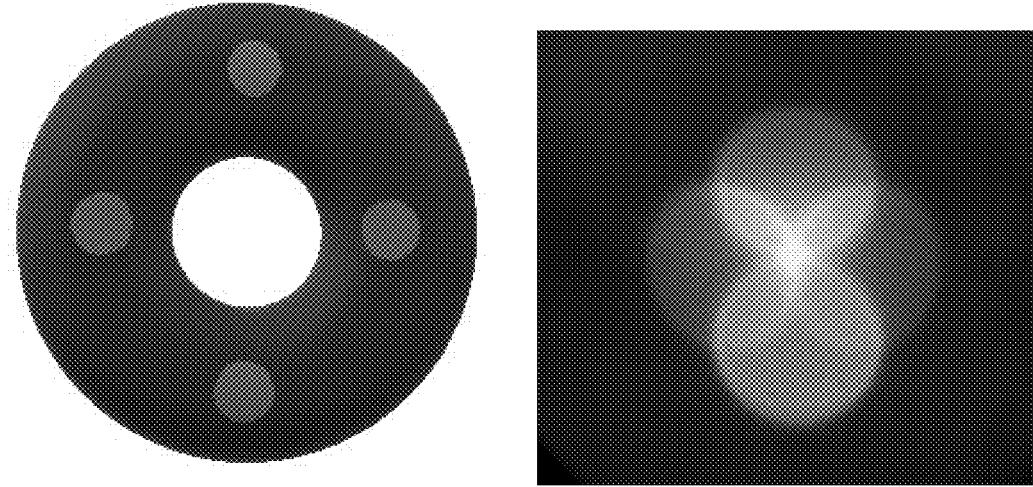
FIG. 10 shows imaging of an illumination beam reflected by a cornea.

The following description is made with respect to the movement of the camera lens (lens barrel) along the Z-axis, which is related to the optimal working distance of the fundus camera. In relation to the above steps S400 to S500, the present embodiment provides a method for adjusting a working distance of a fundus camera, which can be executed by the fundus camera itself or by an electronic device such as a computer or a server (as a control method). The method includes the following steps:

S1, controlling the lens to approach the eyeball and collecting an image, the image being imaging of the illumination beam reflected by the cornea. This step is performed with the lens aligned with the pupil in the XY plane according to the solution of the above embodiment, and in this step, controlling the lens to approach the eyeball means controlling the lens to move in the direction toward the eyeball in the Z axis by the motion assembly. At an initial distance, reflected light irradiated onto the cornea of the eye by the light source of the lighting assembly through an optical lens is imaged on the CMOS to obtain a result as shown in FIG. 10. In this embodiment, the light source includes four light balls arranged on the four sides of the lighting assembly in a cross shape, and correspondingly, four light spots are displayed in the imaging of the light source. In other embodiments, the illumination light source can be shaped as shown in FIG. 8, and light spots in the corresponding shape or arrangement can be displayed in the acquired image.

Figure 11:
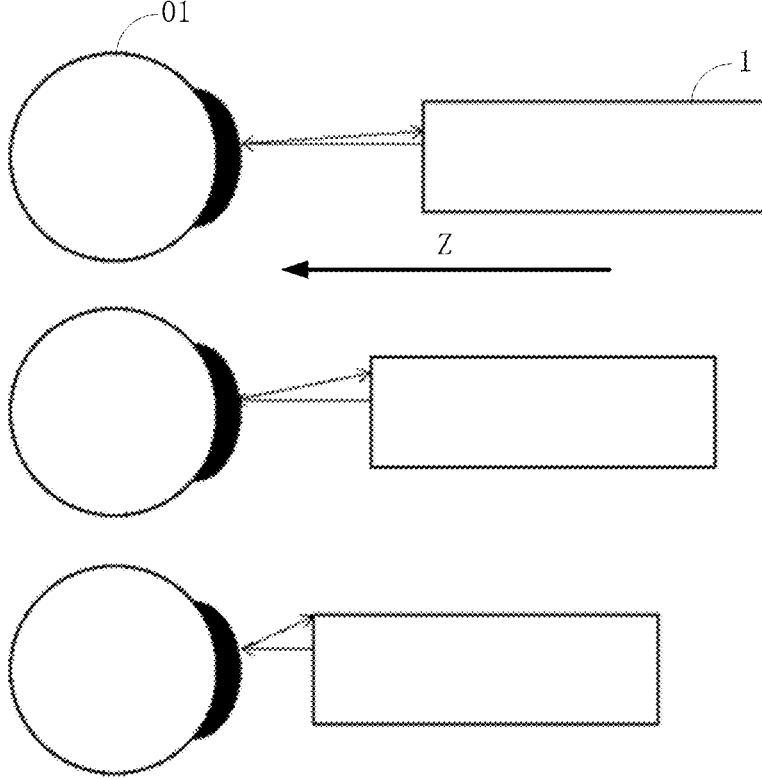
FIG. 11 is a schematic diagram showing a distance between a lens barrel and an eyeball.

S2, detecting whether the feature of the light spot in the image meets a set feature. As shown in FIG. 11, as the lens barrel 1 moves toward the eyeball 01 on the Z axis, cornea reflected light imaging will change. In particular, the position, size and resolution of the imaging is related to a distance between the eye-contacting objective lens and the cornea. The closer the distance is, the larger the included angle between the incident light and the normal line of the cornea is, the heavier the reflected scattering effect is, and the larger the spot size is, the more divergent the spot size is, and the lower the brightness is.

There are various ways to recognize spot features in an image, including, for example, a machine vision algorithm can be used to detect the profile and location of the spot according to graphical features in the image. However, since the resolution, size, etc. of the light spot vary widely, the machine vision algorithm is easy to give a misjudgment, so in a preferred embodiment, a deep learning algorithm is used to solve this problem.

First, imaging of a large number of light spots are acquired, wherein the imaging is acquired by different people at different time and in different directions and distances from the eye-contacting objective lens of the fundus camera. Then, the light spots in each image are labeled, so that training data for training the neural network are obtained. The labeled data are used to train a neural network model (such as a YOLO network), and after training, the recognition result of the neural network model includes a detection box for representing positions and sizes of light spots in the image.

Figure 12:
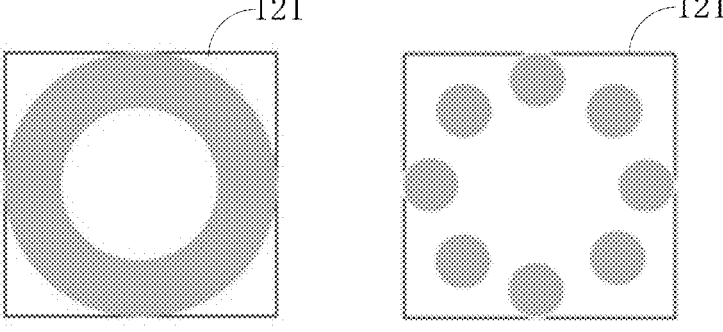
FIG. 12 is a schematic diagram labeling a light spot.

As shown in FIG. 12, in a specific embodiment, a square frame 121 is used in the training data to label the light spots, and the recognition result of the trained neural network model will also be a square detection frame. In other embodiments, a circular box can be used for labeling, and alternatively, other similar labeling methods are possible.

It does not matter what a method is adopted to detect the light spot, as long as it is recognized in this step features of the light spots in a current image meet set features. The set feature can be features relating to size. For example, when the size of a light spot in the image is smaller than the set size, it is determined that the features of the light spots meet the set feature. The set feature can also be disappearance of the light spots. For example, when no light spot can be detected in the image using the machine vision algorithm or the neural network, it is determined that the set feature is met.

If the light spots in the image have the set features, step S3 is performed; otherwise, the procedure returns to step S1 to continue movement of the lens and collection of images.

S3, determining that the working distance is reached. When it is determined that the features of the light spots in the image meet the set features, the distance between the lens and the eyeball at this time can be regarded as the working distance. In a specific embodiment, depending on hardware parameters, a distance compensation can be further performed on the basis of the distance, and the direction and distance value of the compensation are related to the hardware parameters. By way of an example, FIG. 13 shows an image in which the light spots have the set features, and at this time, the distance between the lens 1 and the eyeball 01 is WD; on this basis, the lens is controlled to move continuously to the eyeball direction by a preset distance d to achieve a more accurate working distance WD+.

At the working distance, a fundus image can be shot by further adjusting the focal length. The manner of adjusting the focal length will be described in detail in the following embodiments.

According to the method for adjusting a working distance provided by the embodiment of the invention, the imaging of the illumination beam reflected by the cornea is collected and recognized, and a distance between the lens and the eyeball is judged and adjusted through light spot features in the image, where the working distance can be accurately positioned only by setting an appropriate illumination beam without any additional optics or hardware on the fundus camera, so that the cost of the fundus camera can be reduced, and the working distance adjustment has an improved efficiency.

Considering that the user can slightly rotate his/her head or the like during the movement of the lens toward the eyeball direction, which would cause the lens no longer being in a state of being aligned with the pupil, therefore, the position of the lens will also be adjusted on the XY plane to maintain the alignment with the pupil during the adjustment of the working distance. The present embodiment provides a preferred method for adjusting a working distance, which includes the following steps:

S1A, collecting an imaging of the illumination beam reflected by the cornea;

S2A, calling a neural network to detect light spots in the image, and determining whether light spots are present in the image. When no light spot is present in the image, step S6A is performed; otherwise, step S3A is performed.

S3A, recognizing a central point of the light spot in the image, and determining whether the central point of the light spot is coincided with the central point of the image. The center of the detection frame obtained by the neural network is regarded as the center of the light spot. The central point of the image is regarded as the center of the lens. If the central point of the image coincides with the central point of the spot, the lens is aligned with the pupil, and step S5A is performed, and if the central point of the image does not coincide with the center of the spot, the lens deviates from the alignment position, and step S4A is performed.

S4A, finely adjusting the position of the lens according to a shift between the central point of the light spot and the central point of the image. Detection-adjustment-re-detection is a feedback process, as a preferred embodiment, a smooth adjustment algorithm is used:

$$\text{Adjustment}(i)=a*\text{Shift}(i)+(1-a)\text{Adjustment}(i-1),$$

where Adjustment (i−1) represents displacement of the last lens adjustment, Shift (i) represents an amount of shift (a deviation between the pupil center and the image center), Adjustment (i) represents displacement of the lens which needs to be adjusted this time, and a is a coefficient between 0 and 1. Because the position of the lens is a two-dimensional coordinate on the XY plane, both Adjustment and Shift are two-dimensional vectors.

After the central point of the light spot and the central point of the image are adjusted to coincide with each other, step S5A is executed.

S5A, controlling the lens to move close to the eyeball in order to reduce the distance, and then, returning to step S1A. With repeated executions, the lens gradually approaches the eyeball, and correspondingly, the size of the light spot in the image changes from large to small. In order to accurately capture a critical point for disappearance of the light spot, each frame of image is collected and the above determination and adjustment are performed accordingly until an image with a disappeared light spot is detected.

S6A, controlling the lens to continuously move to the direction close to the eyeball for a preset distance so as to reach the working distance.

In a preferred embodiment, while performing the above adjustment process, it is also detected whether the light spot in the image is complete, and when the light spot is incomplete, such as a half thereof, it means that the user blinks or the eyes are not open, and at this time, the system prompts the user by voice to open the eyes wide and avoid blinking as much as possible.

According to the method for adjusting a working distance provided by the embodiment of the invention, while a distance between the lens and the eyeball is adjusted, the position of the lens is finely adjusted according to a position of the light spot in the image so as to keep the lens aligned with the pupil while the working distance is adjusted. This solution does not require any additional optics device or hardware provided on the fundus camera, and only a suitable illumination beam is needed to accurately position the working distance and keep the lens aligned with the pupil, thereby reducing cost of the fundus camera and increase efficiency of shooting a fundus image.

In addition to the automatic alignment and automatic adjustment of the working distance as described in the above embodiment, an appropriate focal length is needed to shoot a clear fundus image. Hence, a technical solution regarding automatic focal length adjustment is introduced below. With respect to the above step S600, the present embodiment provides a method for adjusting a focal length of a fundus camera, which can be performed by the fundus camera itself or by an electronic device such as a computer or a server (as a control method). The method includes the following steps:

S1, adjusting the focal length and acquiring a fundus image. This step is performed when the lens of the fundus camera is aligned with the pupil and reaches a working distance, the positions of the lens and the eyeball at this time being as shown in FIG. 13. It should be noted that, when images are acquired during the process of adjusting the lens position and the working distance in the above embodiment, it is of course also necessary to set a fixed focal length. For example, when the working distance is adjusted, the focal length can be fixedly adjusted to 0 diopter position. If the subject is normal in refraction, a fundus image can be directly shot when the working distance is adjusted in place. However, in practical application, an actual diopter of the subject needs to be considered, so that an appropriate focal length is set.

Before the fundus camera is exposed to take a fundus image, infrared light is used for imaging in processes such as the automatic alignment and the automatic determination of the working distance, and the light source used for acquiring images is still infrared light at this time. Although the current focal length does not enable the fundus to be imaged clearly, the images acquired at this time have already substantially exhibited characteristics of the fundus in which at least the optic disc can be displayed, and therefore the acquired images are called as fundus images.

S2, recognizing an optic disc region in the fundus image. Since the optic disk region is a region having the largest number of textures and the highest brightness in the fundus, it is most suitable for focusing.

There are a number of ways to recognize the optic disc in a fundus image, including, for example, a machine vision algorithm can be used to detect profile and position of the optic disc according to graphical features in the fundus image. However, since imaging with infrared light is relatively blurred, which brings a significant challenge to recognize the optic disc, the machine vision algorithm tends to give a misjudgment, and thus, a deep learning algorithm is used in a preferred embodiment to solve this problem.

First, a large number of fundus images are acquired, which are fundus images acquired from different persons using different focal lengths. The optic discs in each image are then labeled, thereby acquiring training data for training the neural network. These labeled data are used to train a neural network model (e.g., a YOLO network), and after training, the recognition result of the neural network model includes a detection box for characterizing the position of the optic disc in the fundus image.

Figure 14:
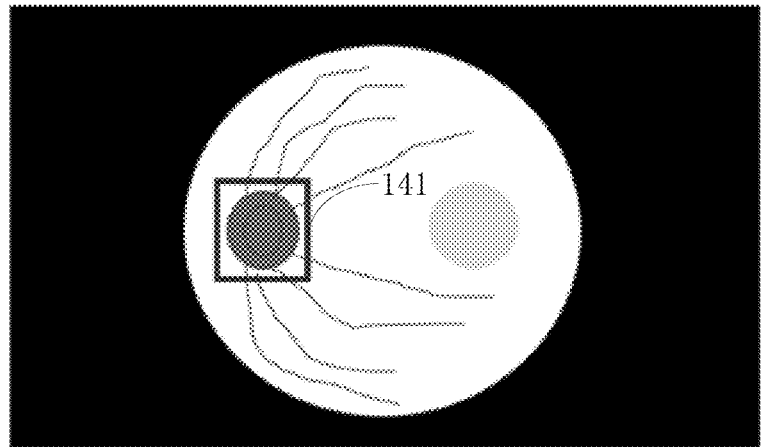
FIG. 14 is a schematic diagram labeling an optic disc.

In one embodiment, as shown in FIG. 14, the optic disc is labeled with a square frame 141 in the training data, and the recognition result of the trained neural network model will also be a square detection frame. In other embodiments, a circular box can be used for labeling, or other similar labeling methods are possible.

S3, determining a shooting focal length according to the resolution of the optic disc region. Specifically, the focal length can be continuously changed in a gradient ascending mode from the initial focal length and a corresponding fundus image is acquired, and then it is judge whether the resolution of the optic disc in the fundus image reaches a preset criterion; once it reaches the preset criterion, it is determined that the current focal length is an optimal focal length, and no further searching is needed; alternatively, all available focal lengths within an adjustable range of the focal length are used and corresponding fundus images are acquired, and then a fundus image with an optic disc having the highest resolution is determined from all fundus images, and it is determined that a focal length at which the image is acquired is an optical focal length.

In one specific embodiment, in a traversal manner, firstly, the focal length is adjusted within a set range of focal lengths of 800-1300 by a first set step length 40 and a first set of fundus images is acquired, and then a fundus image at the focal length of 800, a fundus image at the focal length of 840, a fundus image at the focal length of 880 . . . a fundus image at the focal length of 1300 are obtained. Optic disc regions are recognized in these fundus images, respectively, and the resolution of each fundus image is determined respectively, which, in this embodiment, is an average value calculated from pixel values in the optic disc region. Then, a fundus image having the highest resolution can be determined from the first set of fundus images, and the focal length X (first focal length) used when acquiring this fundus image can be taken as a shooting focal length.

In order to achieve a better shooting effect, the focal length can be further searched. For example, a further traversal is performed near the focal length X, and a second set step length used in this traversal is smaller than the first set step length; for example, the second set step length is 10, so that a second set of fundus images are further obtained, including, a fundus image at a focal length of X+10, a fundus image at a focal length of X+20, a fundus image at a focal length of X−10, a fundus image at a focal length of X−20, and the like. And then, optic disc regions in these fundus images are recognized respectively and the resolution of each fundus image is determined respectively; for example, when it is determined that a fundus image at the focal length of X−20 is a fundus image with the highest resolution, the focal length X−20 (second focal length) is taken as the shooting focal length.

Regarding the range in which the focal length is further searched, as a preferred embodiment, the first focal length X can be taken as a midpoint, with a maximum value being the first focal length X plus the first set step length, and a minimum value being the first focal length X minus the first set step length, i.e., the range is X±40.

According to the focus adjusting method provided by the embodiment of the invention, fundus images are collected at different focal lengths, and it is determined whether the current focal length is suitable for shooting a fundus image through the resolution of the optic disc in the fundus image, wherein an optimal focusing position can be found only by setting an image recognition algorithm without providing any additional optics device or hardware on the fundus camera, so that the cost of the fundus camera can be reduced, and the focus adjusting efficiency can be improved.

Considering that the user can slightly rotate his/her head or the like during the adjustment of the focal length, which would cause the lens no longer being in a state of being in alignment with the pupil. Accordingly, during the process of adjusting the focal length, position of the lens on the XY plane will also be adjusted to keep its alignment with the pupil. In addition, when the process proceeds to this stage, a fundus image is about to be taken, and if the subject blinks or closes his/her eye at this time, the shooting would not be successful, so a detection of blinking and/or eye-closing is also required in the process. The present embodiment provides a preferred method for adjusting the focal length, which includes the following steps:

S1A, acquiring a fundus image using a current focal length.

S2A, determining whether the subject blinks and/or closes his/her eyes based on the fundus image. Prompting is carried out when the subject blinks and/or closes his/her eyes, such as prompting the user not to blink or close eyes and the like by voice, and then the process returns to step S1A; otherwise, step S3A is performed. The blinking and eye-closing detection can also be carried out by a machine vision algorithm or a neural network algorithm. When a subject blinks or closes his/her eyes, the acquired image would be completely black or very blurred, and the characteristics are relatively obvious. Various methods can be employed for detection, which will not be described here.

Figure 15:
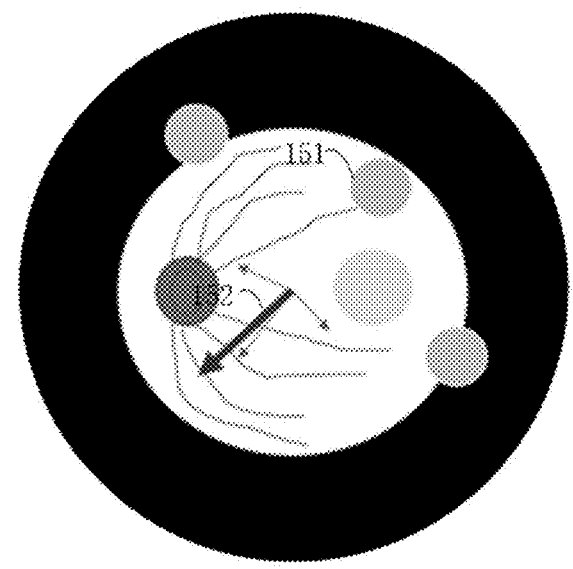
FIG. 15 is a schematic diagram showing movement of a position of a lens according to a light spot when a fundus image is taken.

S3A, recognizing whether a light spot formed by an illumination beam reflected by the cornea is present in the fundus image. Different from the way of keeping the lens aligned with the pupil when the working distance is adjusted in the above embodiment, after the working distance is reached, if the lens and the pupil are in an aligned state, the illumination beam reflected by the cornea should not be in the imaging range, and the above-mentioned light spot would not appear in the fundus image, in particular that no complete imaging of the light spot will appear; even if a light spot appears, it will be a portion of the entire light spot. In one specific embodiment, a light source formed from a plurality of illumination lamps arranged in a circle is used, and a complete light spot is as shown in FIG. 12. If a light spot appears in the fundus image when the focal length is adjusted, it will be the case as shown in FIG. 15 in which only a part of a light spot 151 is present. If the light source itself is a complete circular lamp, this band-shaped object appears in the image.

When the light spot is present in the fundus image, step S4A is performed; otherwise, step S5A is performed.

S4A, finely adjusting the position of the lens based at least on the position of the light spot in order to remove the light spot, such that the lens is kept aligned with the pupil. Light spots appearing at different positions have different sizes and brightness. As a preferred embodiment, a vector offset can be calculated based on the position, size and brightness of the light spot in the image. Taking FIG. 15 as an example, a coordinate system is established with the image center as the origin (0,0), and the image radius is R. An approximately circular area of each light spot 151 is calculated, and in this embodiment, the approximately circular area is the smallest circular area containing the light spot 151. For example, if the center coordinate of the approximately circular area of the ith light spot is (xi, yi), and the radius is ri, it can be concluded that a direction in which the ith light spot needs to move is $vi=(xi, yi)$, and the distance by which it needs to move is $mi=ri+R-$, where $k=xi2+yi2$, and further, it is concluded that the current light spot needs to move by vimi. Then, the amounts by which all the light spots need to move are summed to obtain a vector 152 by which the lens needs to move, and the vector 152 is $\Sigma vm$.

The lens is again brought into alignment with the pupil, and the process returns to step S1A.

S5A, recognizing the optic disc area in the fundus image, and determining whether the resolution of the optic disc area reaches a set criterion. In this embodiment, the optic disc is recognized using the mobilene-yolov3 neural network model, and the optic disc area output from the neural network is an area containing the optic disc and a background. Then, an edge of the optic disc is detected in the optic disc area through an edge detection algorithm (such as sobel, Laplace or the like) to obtain an accurate optic disc image, and an average of the optic disc image is calculated as a resolution value.

For example, it can be determined whether the set criterion is met by comparing the obtained resolution value with a threshold value. If the resolution of the optic disc area does not meet the set criterion, step S6A is executed. If the resolution of the optic disc area has met the set criterion, it is determined that the current focal length is suitable for shooting a fundus image, and then the infrared light can be turned off while the white light is used for exposure to shoot a fundus image.

S6A, adjusting the focal length, and then returning to step S1A. According to the initial focal length used in step S1A, for example, the initial focal length is the minimum value of the adjustable focal lengths, at this time, the focal length is increased according to a fixed step length or a variable step length; otherwise, the focal length is decreased.

After the lens is aligned with the pupil, the optimal working distance is adjusted and the focal length is determined by using the solution provided by each embodiment, a fundus image is shot. When the fundus image is shot, a lighting assembly is needed for exposure (the light source used by the camera of the present embodiment is white light). However, during exposure shooting, the subject can still affect the shooting quality of the fundus image, such as pupil narrowing, eyelid blocking, blinking, light leakage of the face-fitting assembly, and the like. When such conditions appear, unusable areas can appear in the shot fundus image. In order to improve the success rate of shooting, with respect to step S700, the embodiment provides a fundus image shooting method, which can be executed by the fundus camera itself or by an electronic device such as a computer or a server (as a control method), and the method includes the following steps:

S1, keeping state of the lens and shooting a plurality of fundus images. Specifically, in a method according to each of the above embodiments, the lens is fixed at a position in the XY plane to align with the pupil and positioned at a distance in the Z axis, and a fixed focal length is used. While the lens position, the working distance and the focal length remain unchanged, a lighting assembly is exposed and a plurality of fundus images are shot.

S2, respectively determining qualities of the plurality of fundus images. There are various means for analyzing quality of a fundus image. For example, reference can be made to a detection method for a fundus image provided in the Chinese patent document CN 108346149A. In this embodiment, a neural network model is used to analyze the image quality, wherein the neural network model can execute a classification task to classify the image qualities, such as outputting a classification result with high quality or poor quality; alternatively, it can execute a regression prediction task to quantify image qualities, such as outputting 1-10 scores to express an assessment of the image quality.

With respect to training of the model, a large number of white light exposed retinal pictures are collected in advance, the image quality is manually labeled as good or not good (suitable for classification models), or the image quality is scored (e.g., 1 to 10 scores, suitable for regression prediction models). These fundus images and the marks or scores are used as training data to train the neural network model, and the model can be used for recognizing the quality of the fundus image after being converged.

S3, determining whether the quality of each fundus image reaches a set criterion. If any one of the fundus images reaches the set criterion, this fundus image is taken as a shooting result (outputting the shooting result). If none of the qualities of the plurality of fundus images reaches the set criterion, step S4 is performed.

S4, synthesizing one fundus image from a plurality of fundus images as a shooting result. It is possible that each of a plurality of fundus images that are sequentially shot entirely has a poor quality, but each fundus image can have a part area with good quality. In this case, these usable areas are spliced and fused to obtain a complete fundus image with high quality.

A fundus image shooting method is provided according to the embodiment of the invention, the lens state is kept unchanged and a plurality of fundus images are shot, and qualities of the plurality of fundus images are determined respectively. When it is determined that all the fundus images are unusable, the plurality of fundus images are synthesized into one complete fundus image. Even if the subject interferes the shooting process, currently fundus images can be used to obtain a fundus image with high quality, thereby reducing the number of re-shootings, reducing difficulty of use by the user, and increasing success rate of shooting a fundus image.

Further, an embodiment of the present invention provides a fundus image synthesizing method, including the following steps:

S41, obtaining a plurality of fundus images captured with the lens state unchanged. These fundus images have areas of poor quality and areas of good quality, respectively. Of course, if some fundus images are of very poor quality, for example, images with a score of 0 can be all black or all white, these completely unusable images can be removed directly.

S42, extracting high-quality areas in the plurality of fundus images, respectively. In this step, brightness can be calculated from pixel value of the fundus image, and the areas of high brightness and the areas of low brightness are removed by comparison with a brightness threshold value, thereby removing overexposed and underexposed areas to obtain areas of moderate brightness by extraction, i.e., high-quality areas; alternatively, a sharpness can be calculated based on pixel value of the fundus image, and areas of low sharpness are removed by comparison with a sharpness threshold value, thereby removing blurred areas resulting from exposure to obtain high-quality areas; alternatively, high-quality areas can be extracted based on integration of the brightness and the sharpness.

Figure 16:
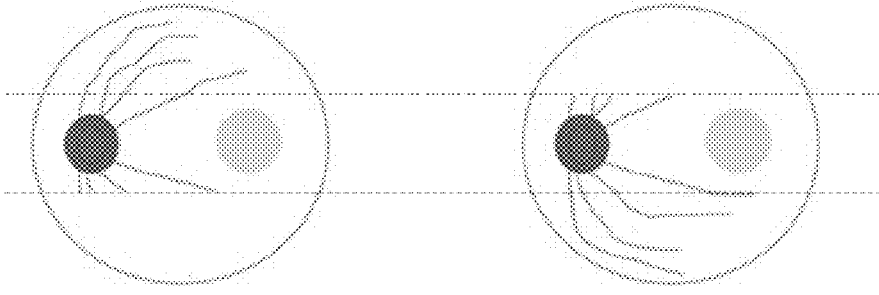
FIG. 16 is a schematic diagram of two fundus images in which an unusable area exists.

Areas extracted based on the actual brightness and/or sharpness of the fundus image are generally areas having irregular boundaries, such as the two high-quality areas as shown in FIG. 16, the left of which is from an upper portion of a fundus image and the right of which is from a lower portion of a fundus image.

In another alternative embodiment, it is also possible to divide each fundus image into meshes in a fixed division manner, and then analyze the quality of each mesh region respectively to extract high-quality meshes, so that high-quality areas with regular boundaries can be obtained.

S43, synthesizing a fundus image from the plurality of high-quality areas. Since each fundus image can have some deviation, in order to more accurately synthesize the fundus image, each fundus image can be mapped to the same coordinate system according to the deviation amount, followed by the splicing and fusing process.

Figure 17:
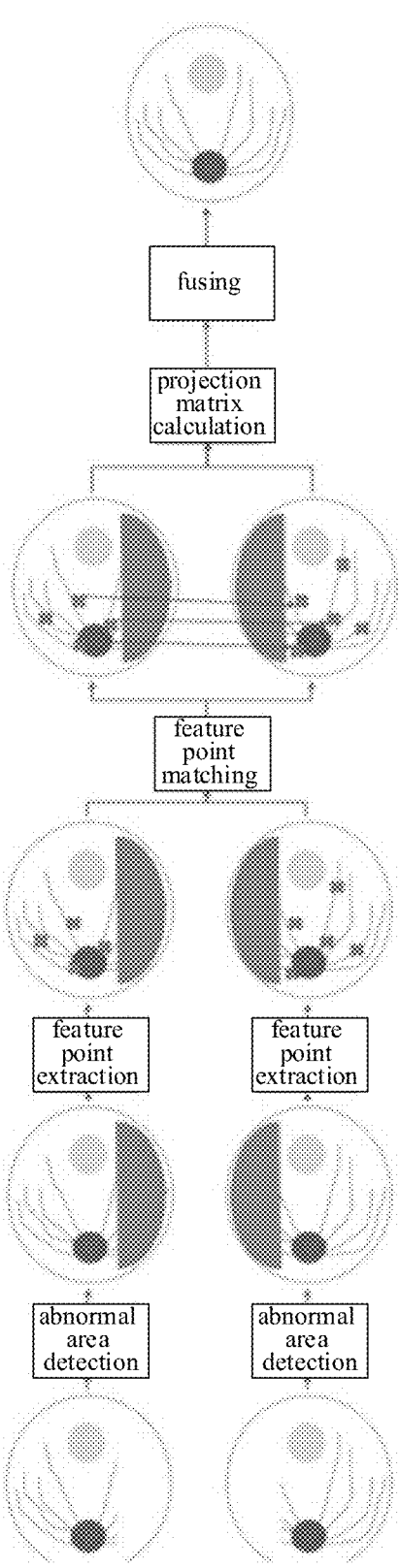
FIG. 17 is a schematic diagram showing a method of synthesizing fundus images.

As a preferred embodiment, as shown in FIG. 17, firstly, abnormal area detection is performed on a plurality of fundus images to extract high-quality areas. In step S43, first, feature points (or referred to as key points) are extracted from a plurality of fundus images respectively, and the feature points can be a prominent position such as the center of the optic disk, the intersection of blood vessels, or the like. Feature point matching is then performed to match feature points between different fundus images, and after matching of these feature points, the matching information is used to calculate the amount of deviation between the respective fundus images (by projection matrix calculation). A plurality of high-quality areas are then mapped into a fundus image according to the amount of shift. For an overlapping portion existing between the plurality of high-quality areas, such as the two areas shown in FIG. 16, the middles of which are repeated, a pixel value of the overlapping portion can be determined using the pixel values of the plurality of high-quality areas and the corresponding weights. This is a fusing process based on weighted average, which can be represented, for example, as $q1/(q1+q2)*image1+q2/(q1+q2)*image2$, where $q1$ represents a weight corresponding to a first high-quality area, $q2$ represents a weight corresponding to a second high quality area, $image1$ represents the first high-quality area, and $image2$ represents the second high-quality area.

The values of the above-mentioned weights are set according to an overall quality of the fundus image, for example the first high-quality area is taken from the first fundus image and the second high-quality area is taken from the second fundus image, while the quality of the first fundus image (for example, the score of the neural network output) obtained according to the above-mentioned quality analysis method is higher than that of the second fundus image, so the corresponding weight $q1$ is greater than $q2$.

The conditions shown in FIGS. 16 and 17 are only examples for explaining the principle of the present solution, and in practical use, more fundus images will be shot so as to ensure that more high-quality areas are extracted as much as possible, and the generated fundus images are complete.

According to the fundus image synthesis method provided by the embodiment of the invention, when a plurality of fundus images shot from a subject have flaws, high-quality areas are respectively extracted from the plurality of fundus images by using this solution, and the high-quality areas are spliced and fused to give a complete fundus image with higher quality, thereby reducing the difficulty of self-photographing the fundus images by a user and increasing the success rate of photographing.

As will be appreciated by one skilled in the art, embodiments of the present invention can be provided as a method, a system, or a computer program product. Accordingly, the present invention can take the form of an entirely hardware embodiment, an entirely software embodiment or an embodiment combining software and hardware aspects. Furthermore, the present invention can take the form of a computer program product embodied on one or more computer-usable storage media (including, but not limited to, disk storage, CD-ROM, optical storage, and the like) having computer-usable program codes embodied therein.

The present invention has been described with reference to flowchart illustrations and/or block diagrams of methods, apparatus (systems), and computer program products according to embodiments of the invention. It will be appreciated that each flow and/or block of the flowchart illustrations and/or block diagrams, and combinations of flows and/or blocks in the flowchart illustrations and/or block diagrams, can be implemented by computer program instructions. These computer program instructions can be provided to a processor of a general purpose computer, special purpose computer, embedded processor, or other programmable data processing apparatus to produce a machine, such that the instructions, which executed via the processor of the computer or other programmable data processing apparatus, create means for implementing the functions specified in the flow(s) of the flowcharts and/or block(s) of the block diagrams.

These computer program instructions can also be stored in a computer-readable memory that can direct a computer or other programmable data processing apparatus to function in a particular manner, such that the instructions stored in the computer-readable memory produce an article of manufacture including instruction means which implement the functions specified in the flow(s) of the flowcharts and/or block(s) of the block diagrams.

These computer program instructions can also be loaded onto a computer or other programmable data processing apparatus to cause a series of operation steps to be performed on the computer or other programmable apparatus to produce a computer implemented process such that the instructions which executed on the computer or other programmable apparatus provide steps for implementing the functions specified in the flow(s) of the flowcharts and/or block(s) of the block diagrams.

It should be appreciated that the above examples are provided only for clarity of illustration and are not intended to limit the embodiments. Variations and modifications in other forms will be apparent to persons skilled in the art in light of the above description. It is neither necessary nor possible to exhaust all embodiments. And obvious variations or modifications derived therefrom are still intended to be within the scope of the invention.

What is claimed is:

1. A fully-automatic photographing method for a fundus image, comprising:

moving a fundus camera lens to align with a pupil;

controlling the lens to approach an eyeball and acquiring an image, wherein the image is an image of an illumination beam reflected by a cornea;

determining a working distance using the image;

adjusting a focal length and collecting a fundus image, and determining a shooting focal length using the fundus image; and shooting the fundus image at the working distance using the shooting focal length;

wherein the method further comprises prior to moving the fundus camera lens to align with the pupil, detecting whether a head of a human body fits a face-fitting assembly of the fundus camera by:

turning off the lighting assembly, and acquiring a first image collected by the lens through a window of the face-fitting assembly:

determining whether the brightness of the first image reaches a set criterion;

when the brightness of the first image reaches the set criterion, turning on the lighting assembly and acquiring a second image collected by the lens through the window of the face-fitting assembly; and determining whether the head of the human body fits the face-fitting assembly according to the second image.

2. The method according to claim 1, further comprising:

prior to the moving of the fundus camera lens to align with the pupil, detecting whether a motion assembly, a lighting assembly and a focusing assembly of the fundus camera are functioning normally.

3. The method according to claim 2, wherein the detecting whether the motion assembly, the lighting assembly and the focusing assembly of the fundus camera are functioning normally comprises:

controlling the motion assembly to adjust the position of the lens, and detecting whether the lens moves to a position of each positioning assembly;

after the lens moved to the position of each positioning assembly, controlling the motion assembly to move the lens to a set position, turning on the lighting assembly and controlling the focusing assembly be adjusted to a first focal length, and shooting to obtain a first image;

determining whether the focusing assembly and the lighting assembly are normal according to image features of the lighting assembly in the first image;

when it is determined the focusing assembly and the lighting assembly are normal, controlling the motion assembly to adjust the lens to a set depth position, controlling the focusing assembly to be adjusted to a second focal length, and shooting a second image; and determining whether an imaging function is normal according to the image features of a subject in the second image.

4. The method according to claim 1, wherein the determining of the working distance using the image comprises:

detecting whether features of a light spot in the image meet set features; and when the features of the light spot meet the set features, determining that the working distance is reached.

5. The method according to claim 1, wherein the determining of the shooting focal length comprises:

recognizing an optic disc area in the fundus image; and determining a focal length for shooting according to a resolution of the optic disc area.

6. The method according to claim 1, wherein the shooting of the fundus image at the working distance using the shooting focal length comprises:

determining whether a size of the pupil is smaller than a size of an annular illumination beam of the lighting assembly of the fundus camera;

when the size of the pupil is smaller than the size of the annular illumination beam, moving the lens to multiple directions respectively to generate an offset from the pupil, such that the annular illumination beam is irradiated partially into the pupil, and shooting a plurality of fundus images; and fusing the plurality of fundus images into one fundus image.

7. The method according to claim 1, wherein the shooting of the fundus image at the working distance using the shooting focal length comprises:

acquiring a plurality of fundus images shot under the condition that the lens state is not changed;

extracting high-quality areas in the plurality of fundus images, respectively; and synthesizing a fundus image using the plurality of high-quality areas.

8. An electronic device comprising:

at least one processor; and a memory communicatively coupled to the at least one processor, wherein the memory stores instructions executable by the processor, the instructions when executed by the at least one processor, to cause the at least one processor to perform the fully-automatic photographing method of claim 1.

9. A fundus camera comprising:

a face-fitting assembly;

a motion assembly;

a focusing assembly;

a lighting assembly;

a lens;

at least one processor; and a memory communicatively coupled to the at least one processor, the memory storing instructions executable by the at least one processor, the instructions when executed by the at least one processor, to cause the at least one processor to perform the fully-automatic photographing method of claim 1.

* * * * *